(12) United States Patent
Frigard et al.

(10) Patent No.: US 12,017,215 B2
(45) Date of Patent: Jun. 25, 2024

(54) MODULAR BIO-PROCESSING UNIT AND A BIO-PROCESSING SYSTEM EMPLOYING PLURAL UNITS

(71) Applicant: Cytiva Sweden AB, Uppsala (SE)

(72) Inventors: Tuomo Valtteri Frigard, Uppsala (SE); Robert Magnusson, Uppsala (SE); Mats Lundkvist, Uppsala (SE); Karl Axel Jakob Liderfelt, Uppsala (SE); Helena Nordvarg, Uppsala (SE); Andreas Torbjorn Lundin, Uppsala (SE); Peter Arne Reffner, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 793 days.

(21) Appl. No.: 16/486,736

(22) PCT Filed: Feb. 27, 2018

(86) PCT No.: PCT/EP2018/054848
§ 371 (c)(1),
(2) Date: Aug. 16, 2019

(87) PCT Pub. No.: WO2018/158273
PCT Pub. Date: Sep. 7, 2018

(65) Prior Publication Data
US 2020/0009557 A1 Jan. 9, 2020

(30) Foreign Application Priority Data

Feb. 28, 2017 (GB) ...................................... 1703233

(51) Int. Cl.
*B01L 3/00* (2006.01)
*B01D 15/10* (2006.01)
*B01D 61/14* (2006.01)

(52) U.S. Cl.
CPC ........ *B01L 3/502715* (2013.01); *B01D 15/10* (2013.01); *B01D 61/145* (2013.01);
(Continued)

(58) Field of Classification Search
CPC ............. B01L 3/5027; B01L 3/502761; B01L 3/502715; B01L 3/502738;
(Continued)

(56) References Cited

U.S. PATENT DOCUMENTS 4,726,929 A    2/1988  Gropper et al.
6,935,772 B2 *  8/2005  Karp ...................... B01D 17/00
                                                        137/550

(Continued)

FOREIGN PATENT DOCUMENTS

EP          0821766 B1       5/2003
JP        2006058112 A       3/2006
(Continued)

OTHER PUBLICATIONS

PCT International Search Report and Written Opinion for PCT Application No. PCT/EP2018/054848 dated May 3, 2018 (10 pages).

(Continued)

*Primary Examiner* — Brian J. Sines
(74) *Attorney, Agent, or Firm* — Eversheds Sutherland (US) LLP

(57) ABSTRACT

Disclosed is a modular bio-processing unit (100) comprising: a housing (110) having one or more internal fluid paths (101), the housing having at least one inlet and at least one outlet (5,10,15,20,25,30,35,40,45,50,55,60,65,70), each in fluid communication with the fluid path or one or more of the fluid paths; one or more sensor elements (120,150,170, 190) operatively associated with the or each path, said sensor(s) elements including elements of one or more of: a
(Continued)

flow sensor, a flow rate sensor, a conductivity sensor, a pressure sensor, a pH sensor, and a light absorbance sensor such as a UV spectroscopic concentration sensor; one or more fluid flow inducing components (140) operatively associated with the or each fluid path; and plural valves (180) for preventing or reducing flow in the or each path, the housing, inlet(s), outlet(s), flow inducing component(s) and valve(s) being arranged to operate together as a bio-processing unit within or substantially within the housing.

10 Claims, 10 Drawing Sheets

(52) U.S. Cl.
CPC ... *B01L 3/502738* (2013.01); *B01L 3/502761* (2013.01); *B01D 2311/2626* (2013.01); *B01D 2315/16* (2013.01); *B01L 2200/028* (2013.01); *B01L 2200/0647* (2013.01); *B01L 2300/0627* (2013.01); *B01L 2300/0809* (2013.01); *B01L 2300/0864* (2013.01); *B01L 2400/06* (2013.01)

(58) Field of Classification Search
CPC ....... B01L 2200/028; B01L 2200/0647; B01L 2300/0627; B01L 2400/06; B01D 15/10
See application file for complete search history.

(56) References Cited

U.S. PATENT DOCUMENTS

| | | | |
|---|---|---|---|
| 2003/0071245 A1* | 4/2003 | Harris, IV | H05K 1/0373 |
| | | | 252/500 |
| 2011/0005932 A1* | 1/2011 | Jovanovich | G01N 27/44721 |
| | | | 204/453 |
| 2012/0093692 A1* | 4/2012 | Blomberg | G01N 30/88 |
| | | | 210/198.2 |
| 2012/0106289 A1 | 5/2012 | Wilt et al. | |
| 2012/0141989 A1 | 6/2012 | Chen et al. | |
| 2014/0116121 A1 | 5/2014 | Zenhausern et al. | |
| 2018/0011005 A1* | 1/2018 | Kirschner | G01N 21/85 |

FOREIGN PATENT DOCUMENTS

| | | | | |
|---|---|---|---|---|
| WO | WO-0228532 A2 * | 4/2002 | | B01J 19/0093 |
| WO | WO-2009119698 A1 * | 10/2009 | | B01L 3/50273 |
| WO | 2010/091406 A2 | 8/2010 | | |
| WO | 2014/081840 A1 | 5/2014 | | |
| WO | 2015/187868 A2 | 12/2015 | | |

OTHER PUBLICATIONS

Great Britain Search Report for GB Application No. 1703233.5 dated Sep. 1, 2017 (4 pages).

* cited by examiner

MODULAR BIO-PROCESSING UNIT AND A BIO-PROCESSING SYSTEM EMPLOYING PLURAL UNITS

CROSS REFERENCE TO RELATED APPLICATIONS

This application claims the priority benefit of PCT/EP2018/054848 filed on Feb. 27, 2018, which claims priority benefit of Great Britain Application No. 1703233.5 filed on Feb. 28, 2017, the entire contents of which are hereby incorporated by reference herein.

TECHNICAL FIELD

The present invention relates to a modular bio-processing unit, for example a cassette for use in the processing of bio-materials, such as aggregated cells, single cells, cell products such as antibodies or other proteins, viruses, bacteria, molecules, or other analogous materials all suspended in a fluid such as a liquid. In particular, but not exclusively, the invention concerns disposable or limited reuse units, providing a low cost integrated bio-processing hardware. The invention further concerns a bio-processing system formed from plural bio-processing units, and methods of operation related to such hardware.

BACKGROUND

Bio-processing is generally a mature technology, with generally accepted and validated processing methodologies. Each process generally has specific associated equipment. However, the cost of that equipment and the inflexibility of those accepted practices are a bather to entry in the industry. Additionally the usual route to a validated process is to start with a pilot scale process before scaling up to increased production. The conventional way of scaling up is increase the size (and cost) of the equipment used, which means that the then scaled up process needs to be revalidated, and the pilot scale equipment is then redundant.

Technically skilled operators are conventionally required at all stages of bio-processing, which adds to costs and is a bather for developing economies to enter the industry. Conventionally bioprocessing equipment comprises discrete hardware components which are interconnected in use by fluid lines. Efforts to simplify individual elements of that hardware abound, but technical solutions to integrate substantially complete bioprocessing hardware at the pilot and up-scaled stages are rare, and would provide a significant technical and commercial advantage.

Most bio-processing is carried out in batches because some of the hardware used can process only a certain volume before it needs to be changed. Each time a batch is processed the equipment has to be sterilized, leading to additional cost.

Some attempts to integrate biological processes have been made at the microfluidic level, but the resultant apparatus is of no use in processing useful amounts of material in bio-processing, for example several ml or more, tens of ml, or liters.

SUMMARY OF THE INVENTION

The object of embodiments of the present invention is to provide a modular bioprocessing unit which has multiple hardware functions combined into a single generally sealed housing so that the unit can be used for multiple bioprocessing functions singly (a unit), or in multiples (a system) when interconnected with other identical or similar units. Thus, other than unavoidably large parts of a bio-processing system such as, fluid reservoirs, chromatography columns, bio-reactors, filters or membranes, all or most of the hardware associated with bio-processing can be formed into one modular unit, where the term 'modular unit' is intended to mean a unit which is adapted to operate with one or more like units, for example where each unit has complementary physical features to effect such a cooperative operation. In order to facilitate low cost manufacture and modularity, such units could have identical or similar external dimensions and form a whole by their common assembly, for example in an external frame or connected in abutting relationship at complementary sides or edges of the units, and/or where inlets and outlets of the units are arranged such that direct abutting contact between units provides a fluid passage between units. Alternatively, or in addition, fluidic interconnections may be made via intermediate tubes in some instances. The use of an external frame may provide for electrical and/or pneumatic power, and electrical signal communication to the units which form a system.

Where multiple units are used together, it is possible to form a continuous integrated bio-processing system where specific steps are undertaken in series and/or in parallel, as explained in more detail below. In particular one unit can be used whilst another is replenished, washed, or otherwise readied for further bio-processing whilst the one unit is processing.

Embodiments of the invention are set out in the independent claims appended hereto, with preferred features set out in the dependent claims. However, the invention extends to any novel feature described, claimed or illustrated herein, and such novel features are not intended to form an indivisible part of a more specific embodiment, even where the novel feature is mentioned only in association with that specific embodiment.

Herein the term 'modular' is intended to encompass hardware capable of being connected directly to, or adjacent to, other similar hardware in a stack, row, column, array, or other pattern, preferably so that the combined hardware functions together, for example in series or parallel as a system, but where a single unconnected piece of hardware can function independently as a unit if needed. This invention is different to so called modular components of a system that comprise different hardware and carry out specific unique functions but that can be put together in numerous ways. Such known modular components cannot be used independently as a bio-processing unit, but rather need to be put together with multiple other different components to make such a system.

More advantages and benefits of the present invention will become readily apparent to the person skilled in the art in view of the detailed description below.

DRAWINGS

The invention will now be described in more detail with reference to the appended drawings, wherein:

FIG. 1a shows a schematic representation of a bio-processing system falling within the scope of the invention;

Figure 2:
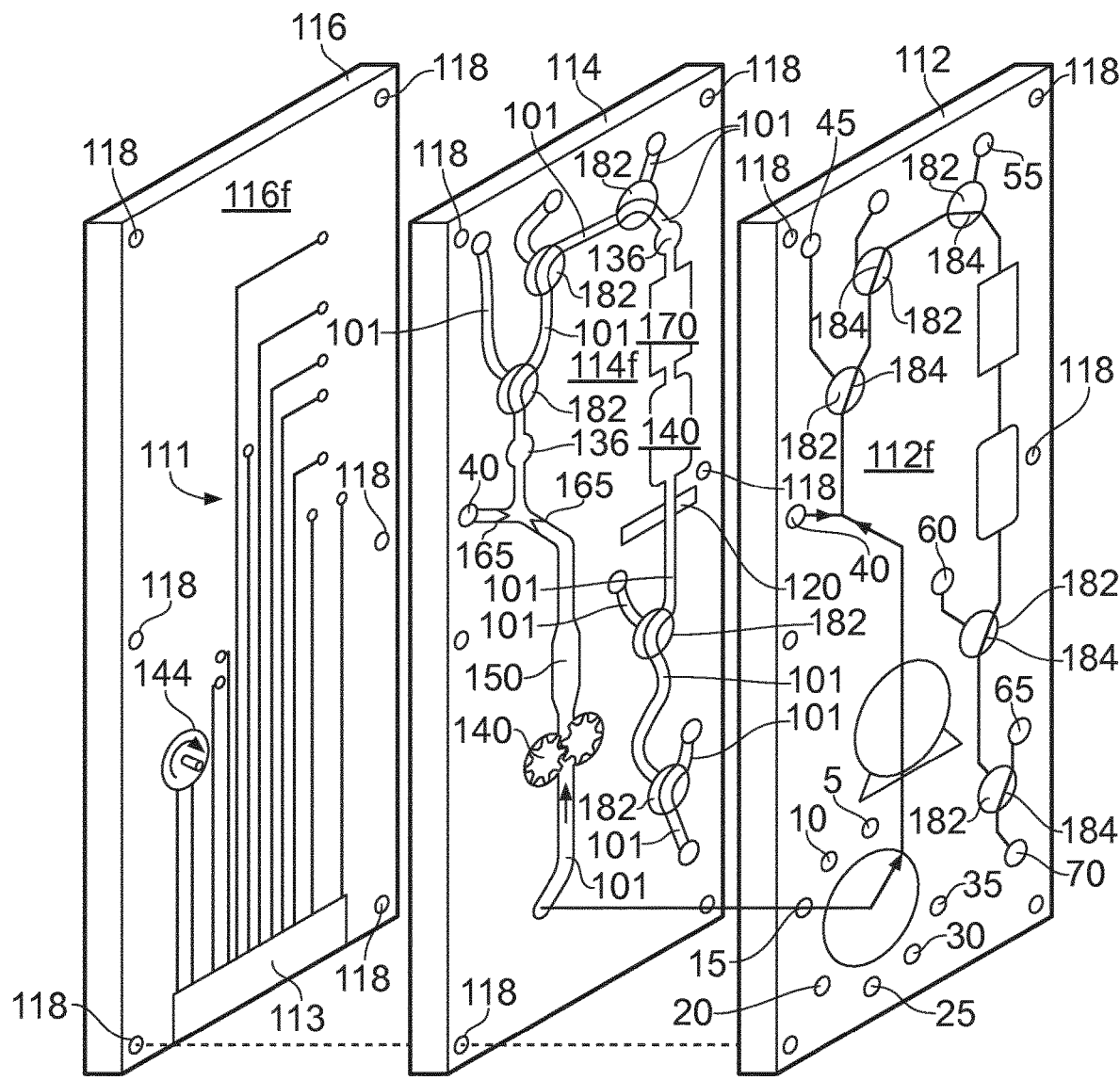
FIG. 2 shows a detailed and exploded view of a bioprocessing unit.
Figure 3:
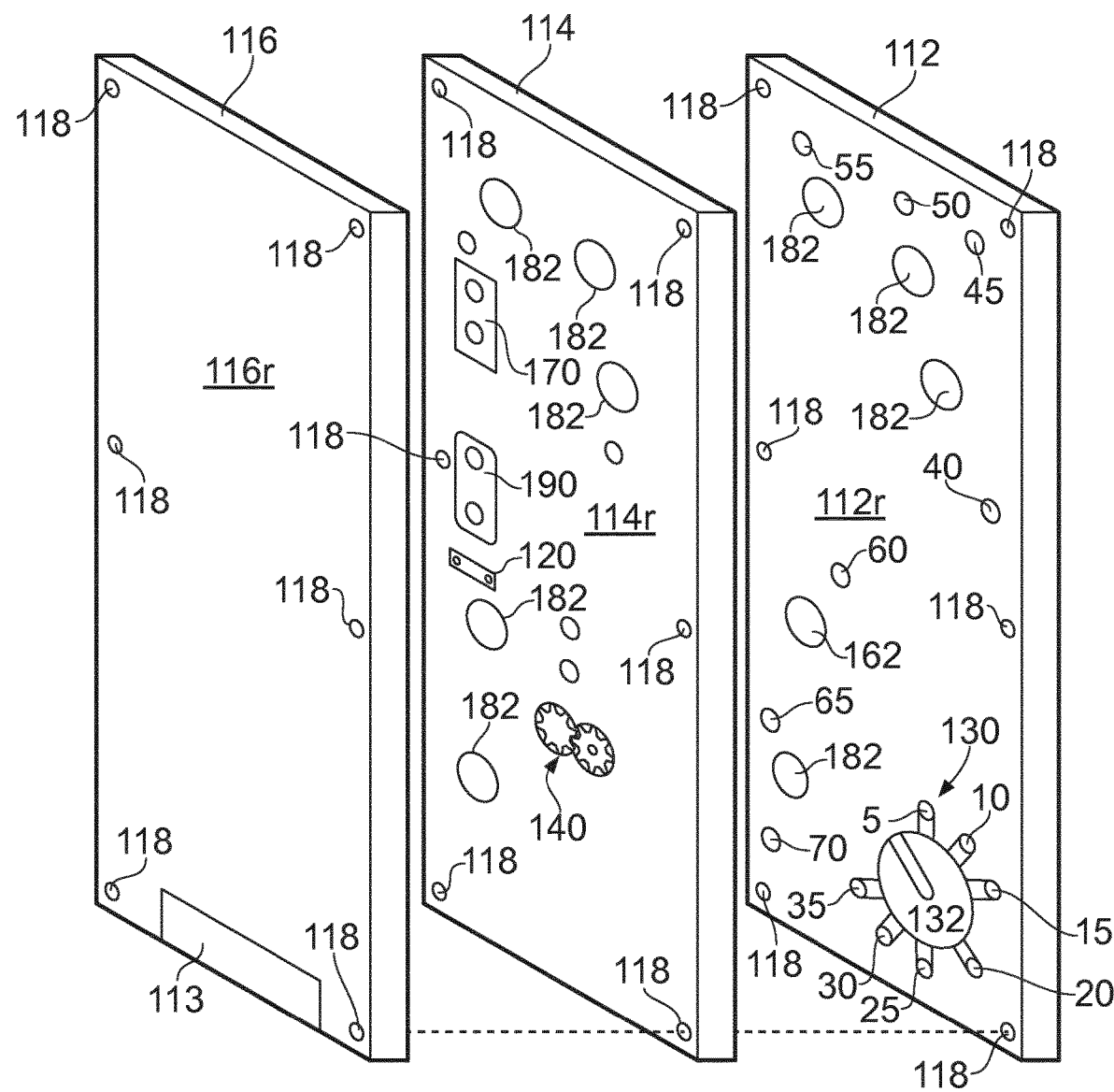
FIG. 3 shows another exploded view of the unit shown in FIG. 2.
Figure 4A:
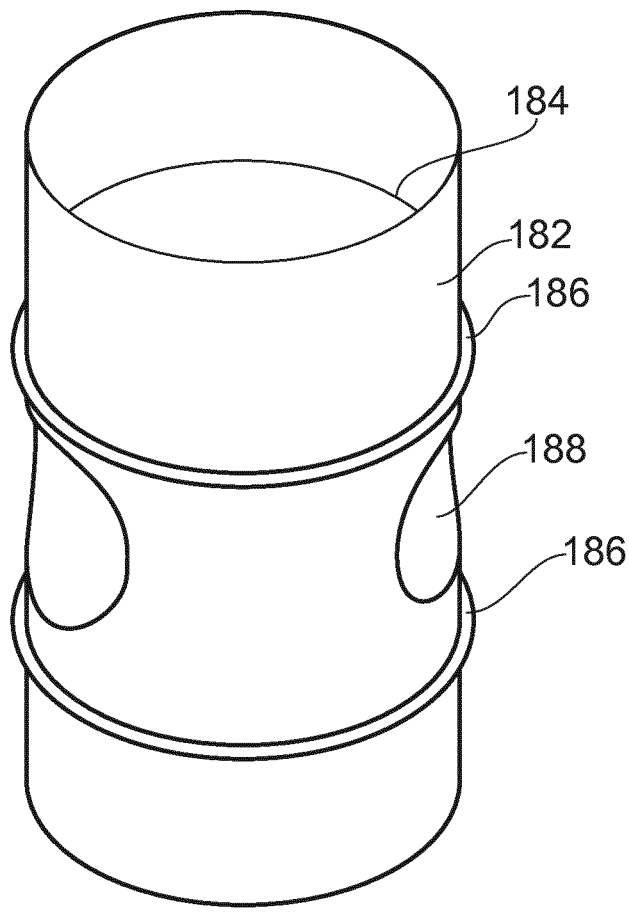
Figure 5:
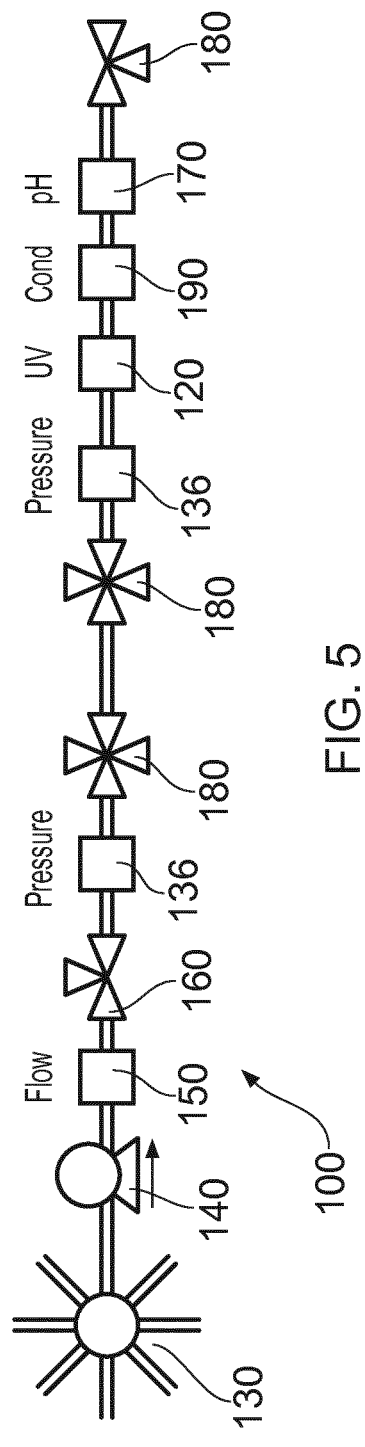
Figure 6:
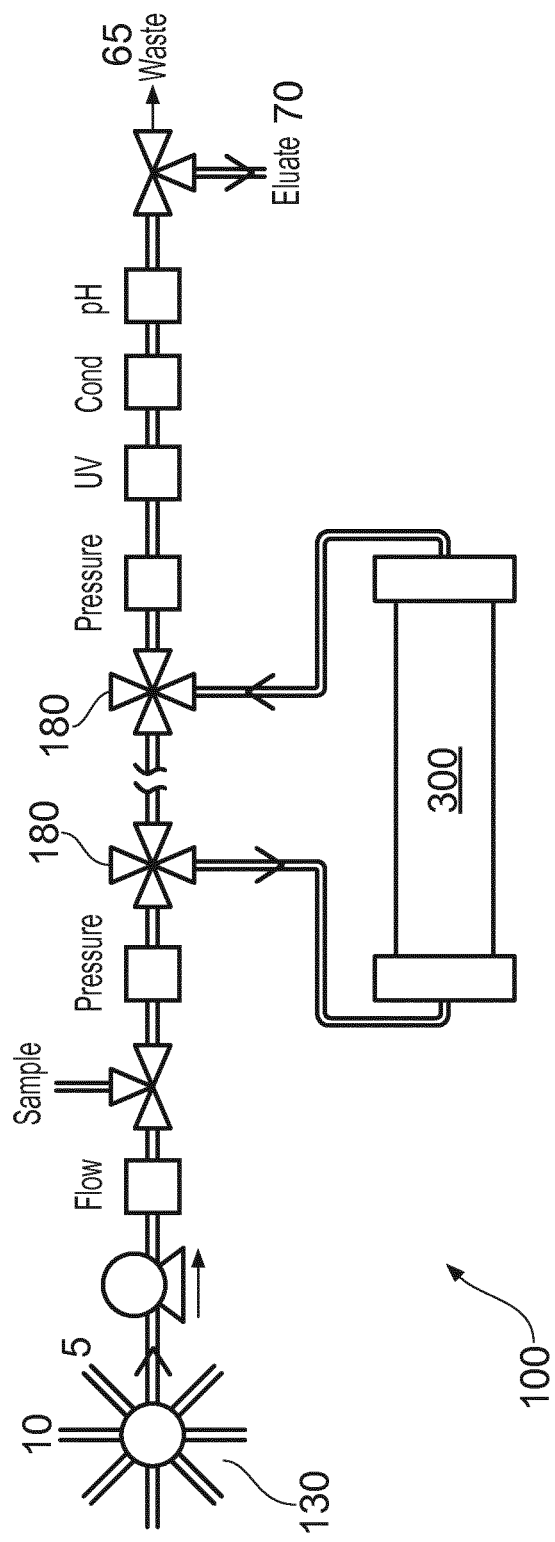
Figure 7:
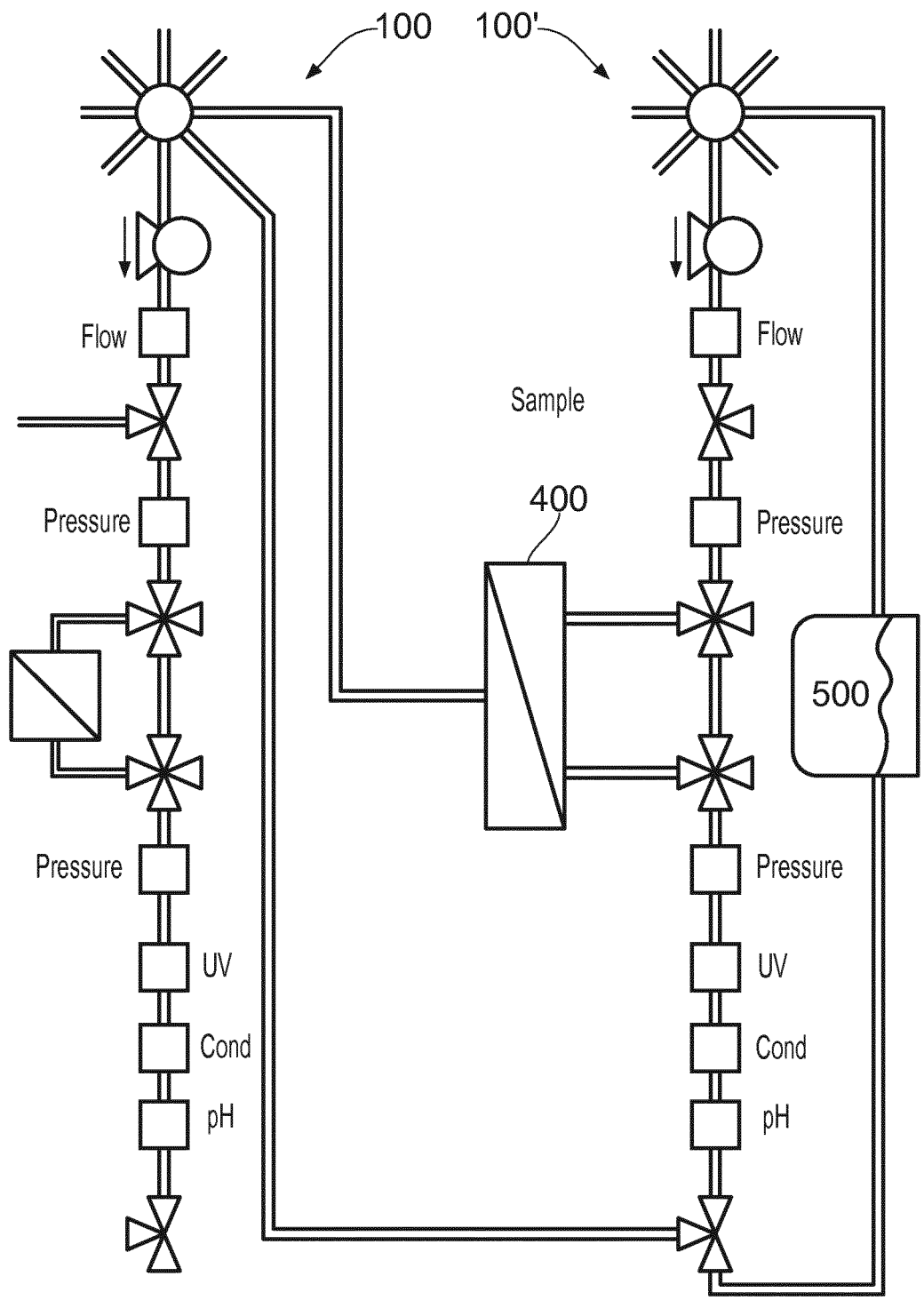
Figure 8:
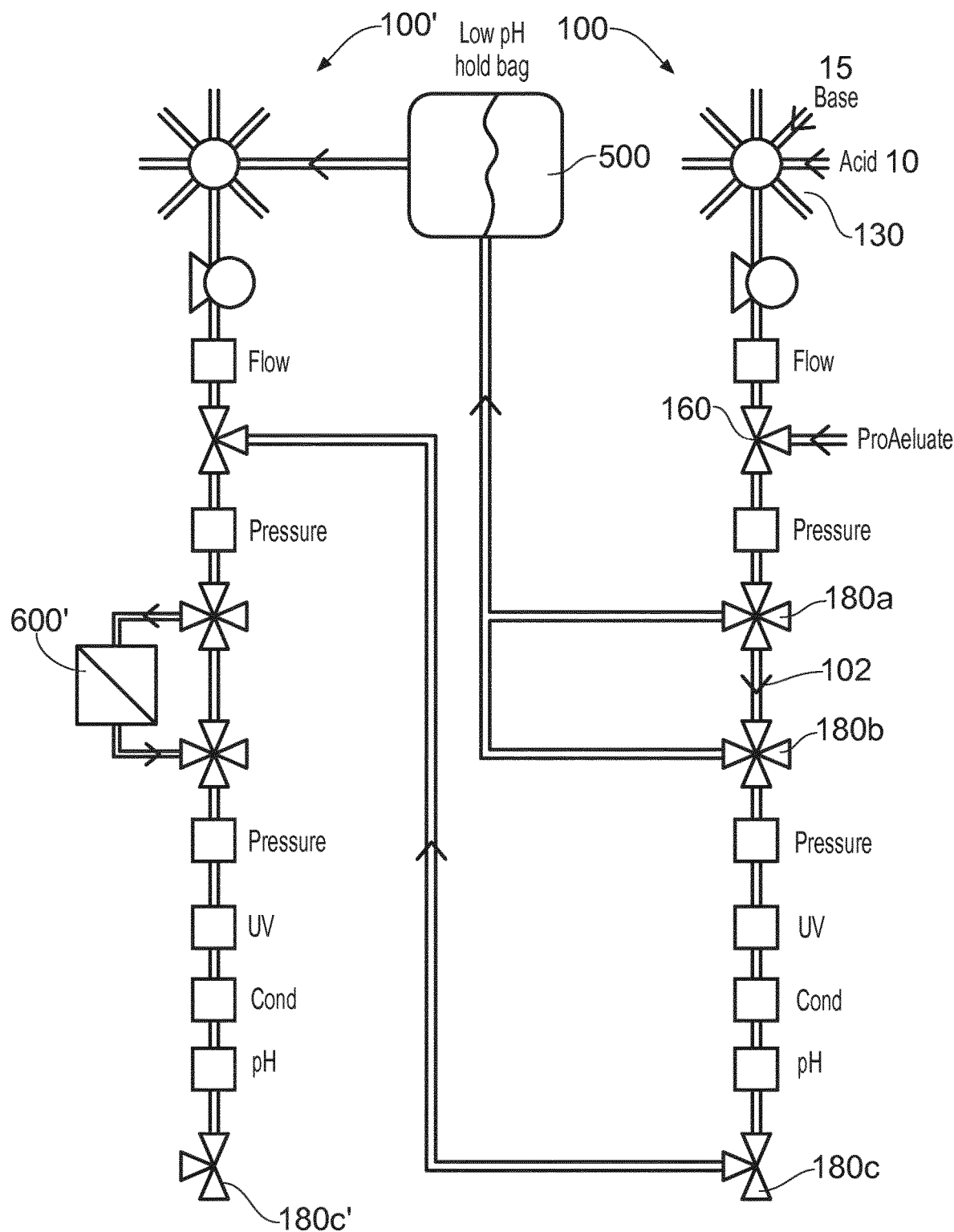
Figure 9:
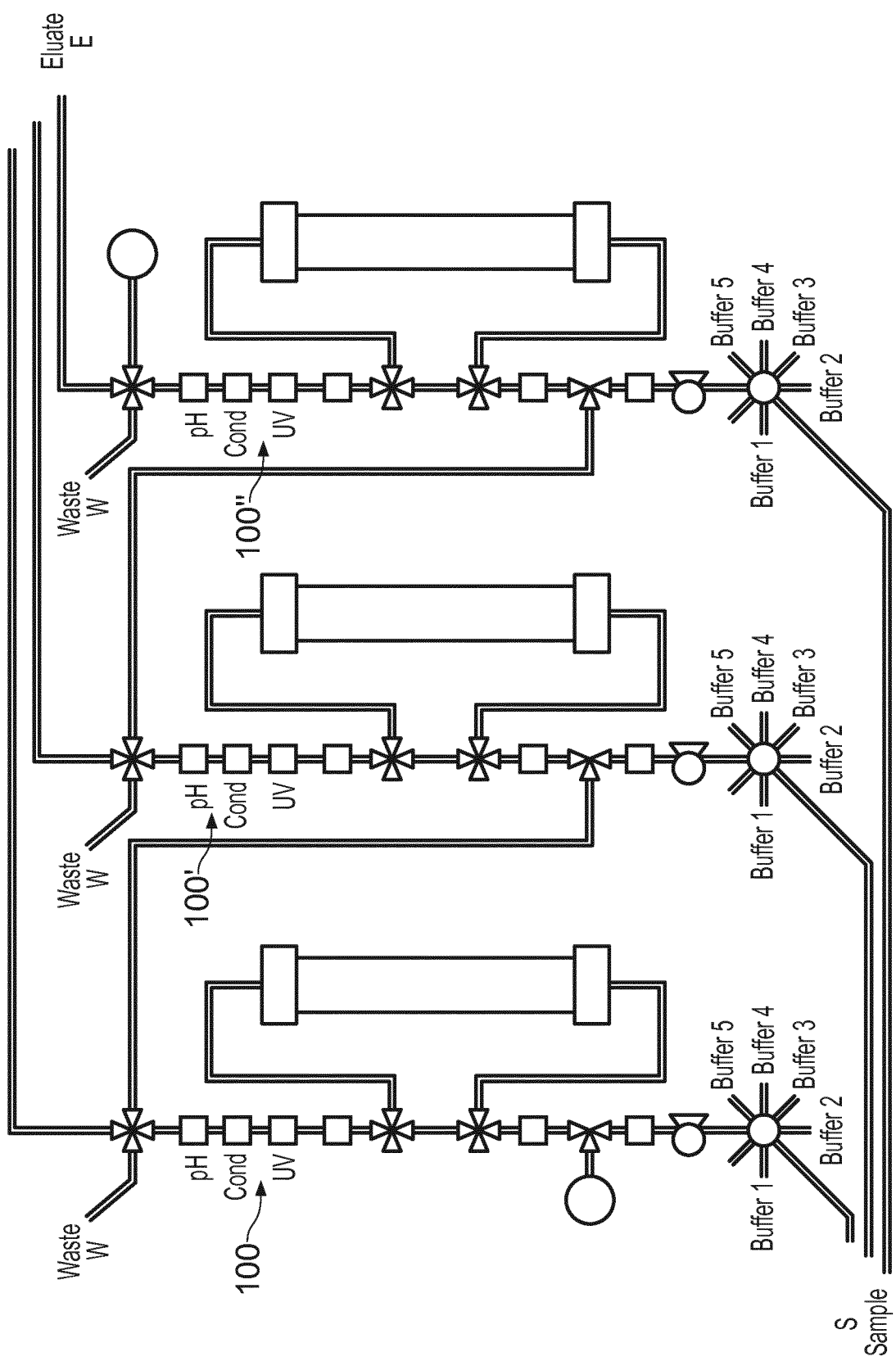
Figure 10:
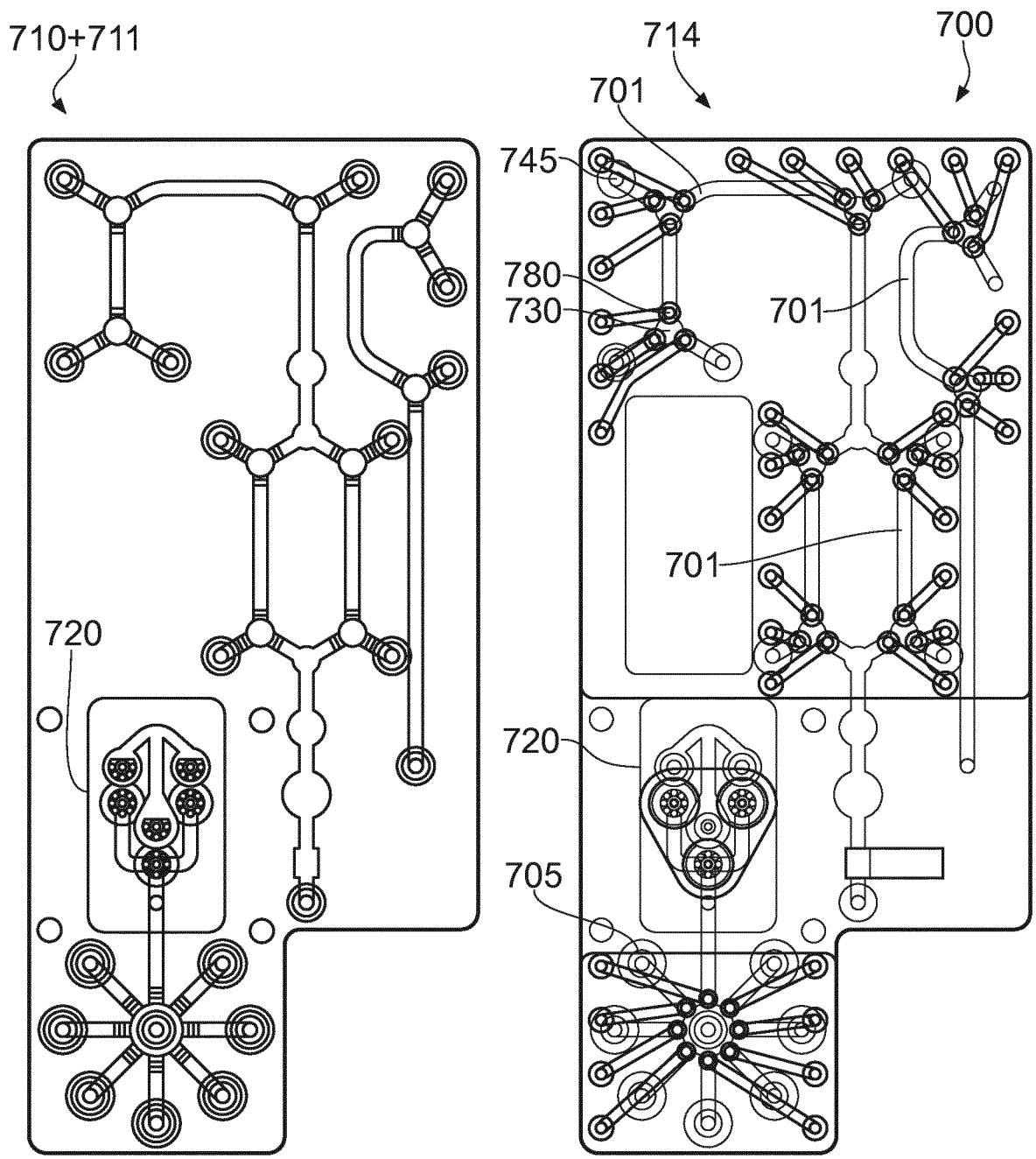
Figure 11:
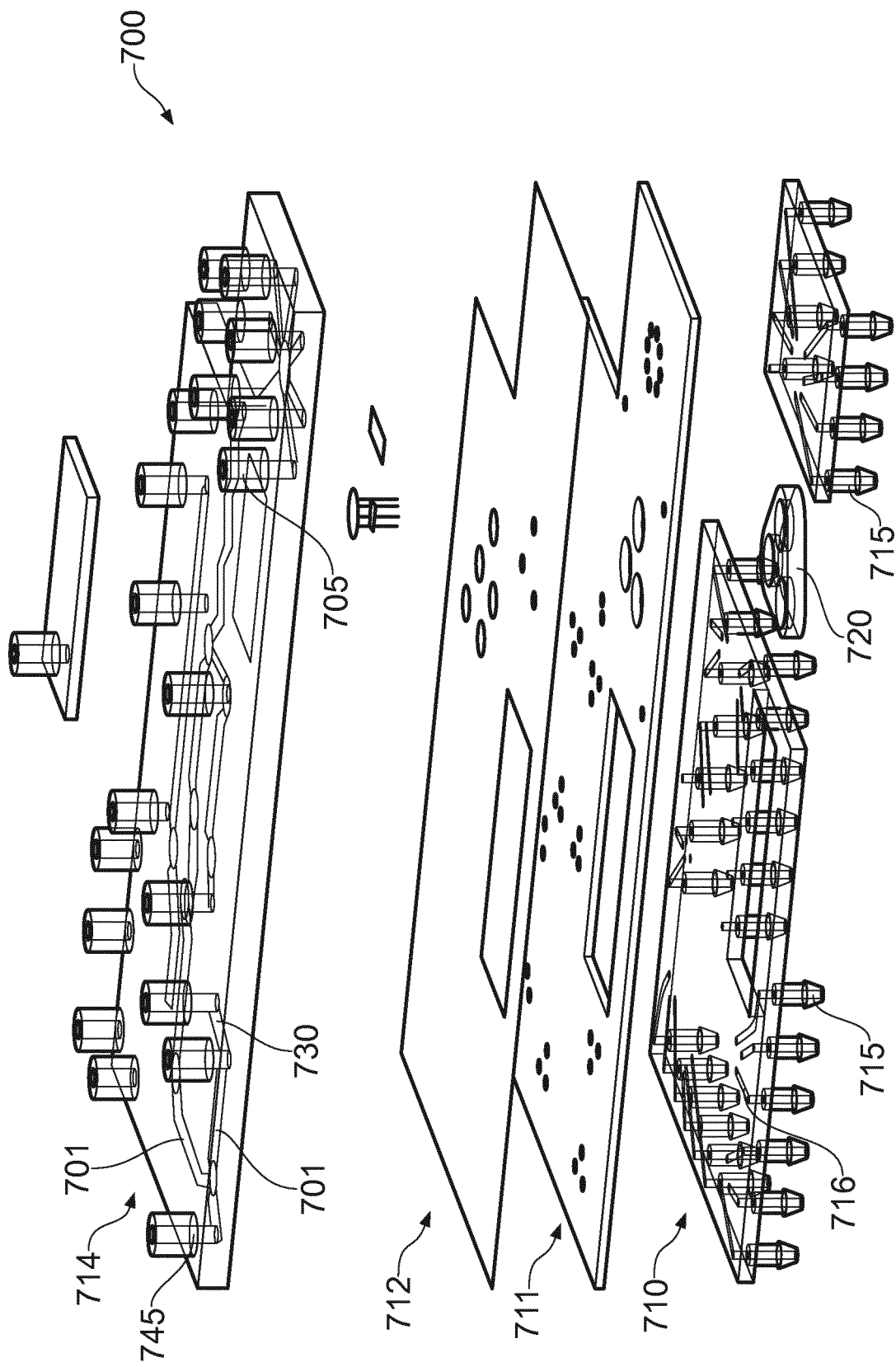

FIGS. 4a, b, c and d each show components of the unit shown in FIGS. 2 and 3;

FIG. 5 shows a further schematic representation of a bio-processing unit;

FIG. 6 shows the bioprocessing unit of FIG. 5 employed in a bio-processing application;

FIGS. 7, 8 and 9 show plural units employed in different bio-processing systems;

FIG. 10 shows layers of an alternative construction of the bio-processing unit; and FIG. 11 shows an exploded pictorial view of the embodiment of FIG. 10.

DETAILED DESCRIPTION

Figure 1:
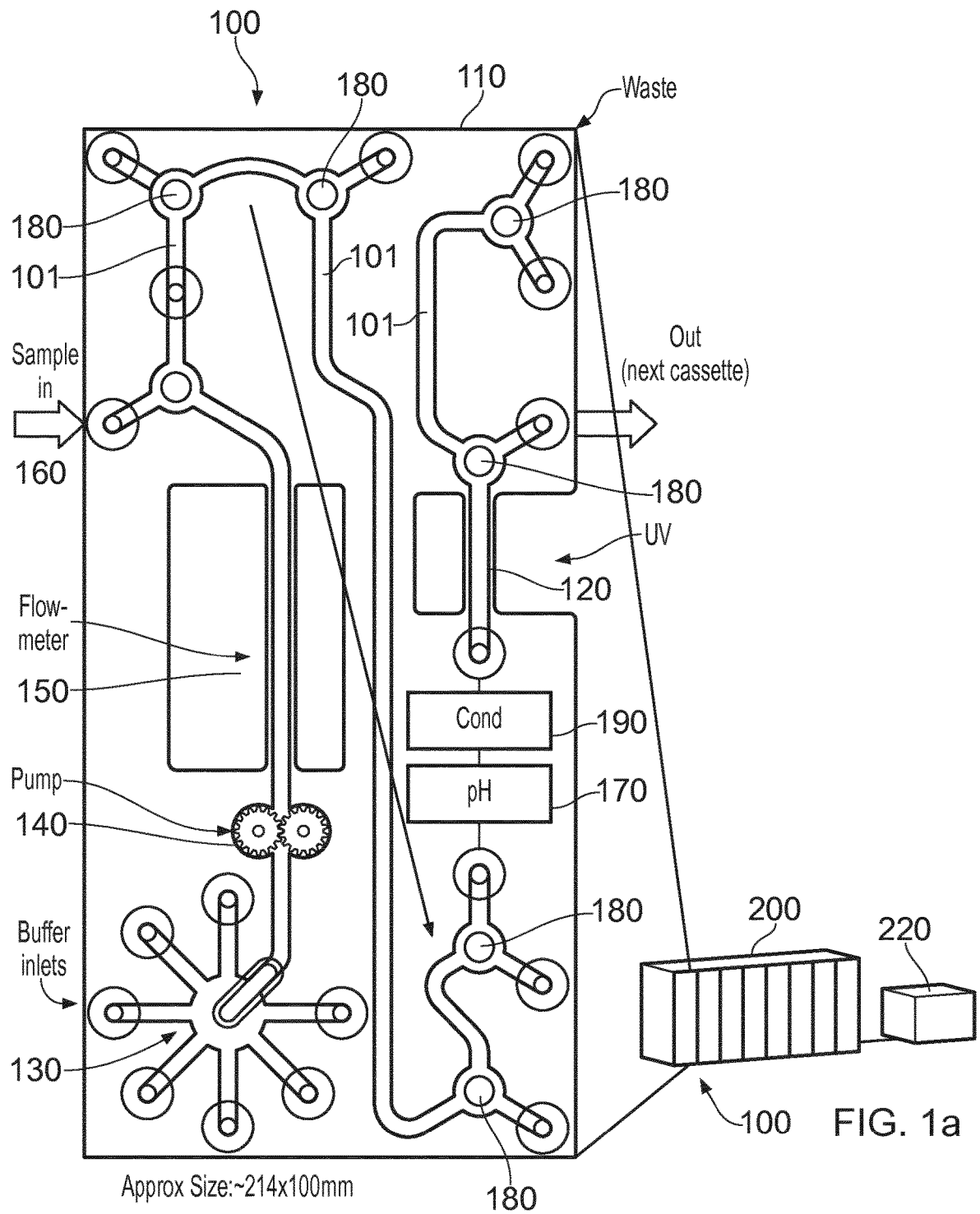
FIG. 1 shows a schematic representation of a bio-processing unit falling within the scope of the invention.

FIG. 1 shows schematically a bio-processing unit 100 which includes a modular housing 110 in the form of a cassette which includes various inlets and outlets described in more detail below. In summary, the unit has integral components comprising or consisting of: a selection valve 130 used to select an input fluid (a liquid or gas) typically a buffer fluid; a fluid flow inducing component in this case a pump 140; a flow meter 150; a sample fluid inlet 160 used typically to introduce a sample fluid into a buffer fluid; various two way valves 180 which have a common construction and are described in more detail below, but have the function of allowing fluid flow entry or egress between the components listed here; a pH sensor 170; a conductivity (Cond') sensor 190; and a UV flow cell spectrophotometer 120 for determining light absorbance characteristics of fluid in the cassette, or an air trap (not referenced). The construction of each of these components is known generally but may be adapted to suit this application as described below. The components of the unit 100 are interconnected internally of the cassette by a fluid path or paths 101 to provide a substantially complete bio-processing unit which can be used for multiple applications. Whilst the order of the components as illustrated is preferred for practical reasons, the order could be changed without significant loss of utility.

In order to that plural units can be brought together to form a bio-processing system, a cassette holder 200 is illustrated in FIG. 1a, which can hold plural units 100 side by side such that their inlets and outlets can be connected either directly where possible, or can be connected by interconnecting fluid paths, such as tubes fitted to quick couplings or the like. If the units are connected directly, then side inlets and outlets e.g. 5, 10, 15 . . . 70, where 'side' means the side in view in FIG. 1 and an opposing side not visible in FIG. 1, may be brought together so that the units, with the help of valves and an external control 220, can be selectably brought into use either one by one, serially together or in parallel to suit the bio-processing function required. Simple annular seals can be employed around the inlets/outlets which connect units together for example in a stack as shown in FIG. 1a. In that case the stack of units provides a three dimension arrangement of fluid paths 101, and where the inlets and outlets are arranged on both sides of the cassette, the valves can be used to control flow into and out of adjacently stacked cassettes. Where supplementary inlets and outlets are needed, for example where a chromatography column is interposed in a fluid flow, then such inlets and outlets can be formed at edges of the units, e.g. the edges of the stacked units shown exposed in FIG. 1a. It will be apparent that edge to edge abutment would also be a practicable arrangement, providing more access for fluidic interconnections by means of interconnecting tubing. In that case intermediate tubing could be used for interconnections between plural units formed into a system, optionally using aseptic connections, for example provided commercially under the trade name INTACT Connectors, by Medinstill Development LLC.

FIGS. 2 and 3 show one example of a construction which could be adopted to make a unit 100. FIG. 2 shows an exploded view of the three main parts used, and FIG. 3 shows the same parts exploded, but viewed from a different angle. The main parts are front plate 112, a middle plate 114, and a back plate 116, each formed from plastics material such as polypropylene or polycarbonate. Each plate is, in use brought into a fluid tight sealing contact with its neighbor to form a fluid tight assembled unit 100, by means of holes 118 which enable fasteners (not shown) to compress the plates into said sealing contact.

The front plate 112 has a front face 112f which includes various selectable inlets 5,10,15,20,25, 30,35, and further ports (inlets or outlets) formed by orifices 40, 45, 50,55,60, 65,70. These ports are illustrated as simple through-apertures, but in practice are likely to be terminated with a quick coupling of known construction, suitable for fluidic connections to external bio-process components, or to other units 100 in a system. In addition, the front face 112f of plate 112 has exposed stems 182 of values 180, which stems include a slot 184 indicating the position of the valves 180. The stem 132 of the selection valve 130 is also exposed in the face 112f and also includes indicia representing the routing position of the selection valve 130. The remaining features shown on face 112f are indicia representing the internal interconnections between the inlets, outlets and valves, and the internal sensors employed.

The rear face 122r of the plate 122 (FIG. 3) shows that the inlets and ports extend through the plate to the rear face, as do the valve stems 182.

Middle plate 114 in use receives or expels liquid flow via the inlets/outlets which extend through front plate 112 to reach the middle plate front surface 114f. Channels 101 formed in a front surface 114f form one or more fluid paths from interconnecting the components of the unit 100 and the various ports 40, 45, 50,55,60,65,70. Whilst the unit flow can be reversed, the preferred direction of flow is as illustrated by the arrows shown within the channels 101. Valve stem 132 can be rotated to select one of the selection valve inlets 5 to 35 to import fluid. Pump 140, in this case a flexible gear pump with one of the gears driven by an electric motor 144, is operable to induce flow. Such a gear pump is described in a co-pending patent application PCT/EP2016/076149 filed 28 Oct. 2016 which disclosure is incorporated herein by reference. The flow meter 150 is positioned immediately downstream of the pump 140. The flow meter is of known construction for example an optical flow meter where light is scattered when a particle crosses the first beam and detecting optics collects the scattered light on a photodetector, which then generates a pulse signal. As the same particle crosses the second beam, the detecting optics collect scattered light on a second photodetector, which converts the incoming light into a second electrical pulse. By measuring the time interval between these pulses, the fluid velocity is calculated as V=D/t where D is the distance between the laser beams and t is the time interval. For a known cross sectional area of the flow path 101, and a known density of fluid, a mass flow rate can be calculated.

The inlet 40 provides a route for additional sample fluid to be injected into the flow path 101. Two one-way valves 165 provide for sample injection to be directed only downstream of the inlet 40. In use fluid flow would next encounter a pressure sensor 136 of known construction, for example a resilient element strained by differential pressure in the fluid path and connected to an optical element deflectable with said resilient element and thereby used to quantify said pressure as the optical element's characteristics change. After the pressure sensor, fluid flowing will encounter one of the valves 180 shown in FIG. 2 with its stem 182 shown in section and thereby showing the arcuate path (188 FIG. 4*a*) through the stem which path can be diverted by rotation of the valve stem, to reposition the path into one of three flowing positions. Thereby fluid can flow toward the remaining components of the cassette 100 as illustrated or out through the adjacent path leading to the orifice 45. The same description applies to the two other valves immediately downstream of the valve described above. Pressurized flow could be brought in to the orifices 45, 50, and 55 of course, and then directed by the valves 180.

Further downstream is another pressure sensor 136, a pH sensor 170, a conductivity sensor 190 and a UV light spectrophotometric flow cell for measuring light absorbance of fluids, all having known constructions. A further two valves 180 allow for fluid flows to be diverted in use, for example in response to the outputs of the sensors mentioned.

The back plate 116 has a front face 116*f* which carries electrical conductors 111 for carrying power and signals to respective sensors, and has an opening for holding the pump motor 144. The plate 116 also carries a connector block 113 for connecting said conductors to an external control 220 (FIG. 1) via complementary connectors (not shown) located in the holder 200. The conductors make contract with complementary conducting elements on the rear face 114*r* of the middle plate 114 at assembly of the plates 116, 114 and 112. Also, the stem of motor 144 engages on assembly with the driven gear of pump 140.

Figure 4B:
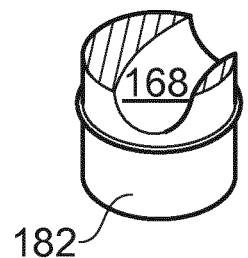

FIGS. 4*a* and 4*b* show enlarged views of one of the valve stems 182, wherein the slot 182 is shown more clearly which aligns with an arcuate duct 188 in the stem, each side of which is a seal 186 for sealing against a respective stem orifice in the front and middle plates.

Figure 4C:
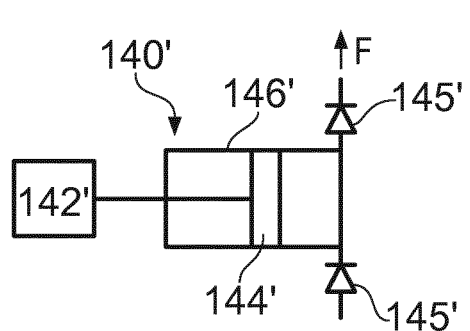

FIG. 4*c* shows schematically an alternative pump construction 140', wherein an actuator 142' drives a piston 144' within a chamber 146' in a reciprocating manner, and two one-way valves 145' restrict flow in in a flow path F to one direction indicated by arrow F. That construction provides a lower cost solution to the gear pump 140 described above. The actuator could be electrically or pneumatically driven for example.

Figure 4D:
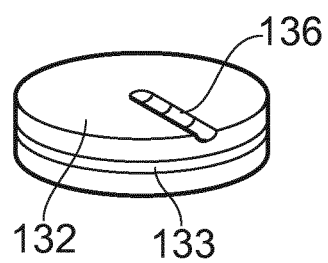

FIG. 4*d* shows an enlarged view the selection valve stem 132, wherein a rear face of the stem (viewable on face 112*r* in FIG. 3) is uppermost, and includes a selection valve channel 136 for diverting fluid flow from the desired inlet to the internal fluid flow path formed in face 114*f* and positioned at the center of rotation of the stem 132 in this case. An annular seal 133 inhibits valve leakage.

It should be noted that one or more of the sensors 120, 136, 170 and 190 could be replaced by an inlet and an outlet, with or without a valve 180, arranged to divert any fluid flow to a remote sensor with equivalent functionality to the sensor replaced. In that case, it could be possible to reuse such a remote sensor after disposal of the remainder of the unit 100.

The invention is not to be seen as limited by the embodiments described above, but can be varied within the scope of the appended claims as is readily apparent to the person skilled in the art. For instance, manually operable valves 130 and 180 have been described and illustrated, however it is envisaged that other valve constructions could be used which are equally low cost and thereby suitable for disposable units. One such valve construction is a pneumatically operable diaphragm valve for example of the type described in co-pending patent application US2014/071405 where pneumatic control is used to open and close valves whereby directing fluid flow in place of the valves 180. That that case the pneumatic supply used to drive the valves could be used to drive the pump 140' also. A connector block similar to the connector block 113, would be used if pneumatic power and or valve signals were employed. Whilst it is possible to manually control the valve operations, as described above, automated control, for example via controller 220 is preferred. In that instance pneumatic valves or motorized valves could be used in place of the manually selectable valves 180 and 130 illustrated. In addition, it should be noted that the specific embodiments described above could be constructed in various ways other than the construction shown. For example, the electrical power connections 111, could be omitted and the sensors could be made internally powered for example by means of batteries and thereby need just signal connections. The sensors could be made RF activated, and would then need no power other than that provided by the RF energy used to induce a sensor response from the relevant sensor. Thereby both signal and power connections could be omitted, other than a power/pneumatic supply to the pump 140. Since the units are formed wholly or predominantly from plastics material and can be supplied for use in substantially sterile hermetically sealed packaging, then they are suitable as single use devices.

For low cost a single generic cassette 100 could be made, but with different throughput capacity, for example different channel 101 cross sectional areas and different pump capacities. In that way, scale up of the system is possible without the need to revalidate the process. In another alternative the cassettes could be optimized to suit a predefined bio-processing function, for example cassettes designed specifically for chromatography, or filtration, or virus inactivation etc. and thereby such specialized cassettes may omit sensors or pumps not used for that particular application. However, the external configuration of the cassette can be kept universal so that all cassettes fit a common external holder, such as holder 200.

FIG. 5 illustrates the unit 100 as a functional schematic representation, where the unit components are set out in a linear series. In this variant, the UV light absorbance meter is upstream of the conductivity and pH sensors but this merely illustrates that the exact order of the components could be different to the order which is illustrated in FIGS. 1 to 3.

FIG. 6 shows the unit of FIG. 5 employed with a chromatography column, filter, membrane or other external component 300. The direction of flow in use is illustrated by the various arrows and in particular the flow is diverted through the external component 300 by valves 180. Selection valve 130 can be used initially to take in fluids at inlet 5 for example from a cell culture vessel or the like (not shown), process those fluids and deliver them to outlet 70 for as long as the sensors indicate that a desired fluid is available at the outlet 70. Before and/or after that period, unwanted fluids can be delivered to the outlet 65 as waste etc. Cleaning fluid or secondary fluids can then be taken in at inlet 10 and if necessary delivered to the waste outlet 65.

FIG. 7 shows a second application of the unit 100, in this instance used together with a second unit 100' to form a bioprocessing system, along with a filtration device 400 and a holding tank 500. With this arrangement, it is possible to perform conditioning steps e.g. filtration or liquid conditioning between chromatography steps. Sample treatment by means of ultrafiltration or diafiltration or cross flow filtration and/or liquid conditioning an also be performed selectively.

FIG. 8 shows the unit 100, together with a second unit 100' for viral inactivation, where a protein (called protein A in this case) can be introduced from a chromatography apparatus or culture volume into port 160 along with a base from port 15 and diverted to a holding tank 500 for viral inactivation. The pH of the tank can be adjusted with the addition of an acid from port 10. The fluid in holding tank 500 can be processed in a second unit 100' after a time in the tank 500, by diverting flow into a cross flow filter 600' and out via a valve 180c'. the viral inactivation step can be omitted by diverting fluids along path 102 to ward a valve 180c and into the second unit 100' for filtration at filter 600'.

FIG. 9 shows three units 100, 100' and 100" used together for three stages of a chromatographic bio-processing of a sample S, for example a sample fluid containing a protein of interest which is to be concentrated, and including three chromatography columns 300, 300' and 300". Operation could take place serially i.e. using one column after the other for greater concentration of the eluted product at output E, or sequentially, i.e. one unit is operable until its chromatography media is saturated or fully bound and the breakthrough is captured at the second column until then the flow is switched to the next unit and so on, or continuously i.e. in that sequential manner, but additional with a purifying step for a resting column to make it ready to further operation when needed. In each case the valves used can be switched accordingly and waste products can be diverted to a waste path W rather than to the output E.

FIGS. 10 and 11 show another embodiment of a bio-processing unit 700, which can function in the same manner as the bio-processing units described above. Therein, two principal layers, a fluidic layer 714 and a pneumatic layer 710 are illustrated, separated by a support layer 711 and a flexible elastomeric layer 712. The fluidic layer 714 has fluid conduits 701, only some of which are referenced, providing inlets and outlets as described above only two of which 705-745 are referenced. The direction of flow at junctions 730 in said paths is controlled by go/no-go membrane valves 780, only one of which is referenced, for example, one formed at each leg of the junction 730. By opening a pair of valves in desired legs of the junction corresponding to the desired fluid flow path, then fluid can be directed correspondingly only along those open legs. Flow can be split by opening three or more membrane valves. Flow can be partially restricted by offering a fractional gas pressure or vacuum in a pneumatic channel. Pulsed pressure or vacuum could also be employed to partially restrict flow. Gas pressure/vacuum pulse width modulation can also be used to variably restrict flow. Pneumatic layer 710 and support layer 711 together direct gas pressure and/or vacuum via pneumatic channels 716, to deflect an associated portion of the membrane 712, and thereby to effect the opening or closing of respective fluid paths 701 for valving, as mentioned immediately above. Each pneumatic channel has a respective nipple 715, for a suitable pressured gas supply and/or vacuum connection.

In order to induce fluid flow in the fluid channels 701 a pump 720 is provided, in this case formed from 3 chambers which are compressible or expandable. Preferably, each chamber has an inlet and outlet and a one-way valve at its respective inlet and outlet, and so the arrangement for each chamber is similar to the pump 140 shown in FIG. 4c. However, the pump will work with just a pair of one way valves serving one or more chambers. The pump may be powered electrically via solenoids, or pneumatically using the same pressurized gas supply that will operate the valves.

The above examples should not be seen as limiting. It is envisaged that any of the following bioprocessing steps could be performed with the unit described above, either operating singly or together with multiple units as system: cell removal by filtration of a liquid culture medium comprising a recombinant therapeutic protein or the like; chromatographic capture using additional apparatus such as a chromatographic column or separation membrane for capturing cells, viruses or recombinant therapeutic protein from a liquid culture medium; viral inactivation; solution conditioning; one or more polishing steps via chromatographic columns or membranes; ultrafiltration/diafiltration after chromatographic purification; sample/solution conditioning; and/or providing means for a column switching chromatography. Where multiple units are used to form a system, the controller 220 is operable to control the operating sequence of the valves and pumps used, in accordance with a predefined program, where necessary modified by data representative of sensor readings. It is further possible that each unit has its own control and that the units are connectable via a communication bus, so that the units communicate, for example, one unit being designated as a master unit, and the remaining unit(s) acting as slave units.

Advantages of the described embodiments include: a small foot-print due to a compact design; a functionally closed system at all stages of processing; an easily reconfigurable arrangement for different needs, including a single control which enables more simple software for, integrated, continuous or semi-continuous processes; an easily scalable system where parallel units can be employed to provide additional bio-processing volumes providing more than 50 ml batches of product, e.g. hundreds of ml or even liters of product; and an easily transportable system. Embodiments are particularly suitable for production of therapeutic protein drug substances, such as recombinant proteins expressed by cultured mammalian cells, and for single use applications where the low-cost nature of the embodiments can make disposal after a single use commercially possible. Low cost can be aided by forming the housing parts of the units described substantially from plastics materials and heat bonding also called diffusion bonding. Sealing between layers of a unit can be made using low cost gaskets, or a continuous run of diffusion bonding. It is possible to bond peripheral edges of a unit to provide a hermetically sealed unit which will remain sterile before use, where peel-off seals can be used over fluid inlets/outlets.

The invention claimed is:

1. A modular bio-processing unit operable with like units to provide a bio-processing system, the unit comprising:
   a housing having at least one internal fluid path, the housing having at least one inlet and at least one outlet, each in fluid communication with the at least one fluid path;
   at least one sensor element operatively associated with the at least one internal fluid path, the at least one sensor element including elements of one or more of: a flow rate or flow direction sensor, a conductivity sensor, a pressure sensor, a pH sensor, an air trap and a light absorbance sensor;
   at least one fluid flow inducing component operatively associated with the at least one internal fluid path; and
   plural valves for preventing or reducing flow in the at least one internal fluid path,
   wherein the unit comprises a fluidic layer comprising the at least one internal fluid path and a pneumatic layer separated by a support layer, and a flexible elastomeric layer provided between said support layer and said fluidic layer.

2. The modular bio-processing unit of claim 1, wherein the unit includes a selection valve for selecting input into the at least one internal fluid path from plural sources.

3. The modular bio-processing unit of claim 2, wherein the at least one flow inducing component provides a direction of intended flow in the unit, and wherein the selection valve is upstream of the at least one flow inducing component and said at least one sensor element and said plural valves and downstream of the selection valve.

4. The modular bio-processing unit of claim 1, wherein the housing has an external cassette configuration arranged to fit within or adjacent a cassette holder.

5. Two or more modular bio-processing units each of claim 1, wherein the two or more units have a different bio-processing capacity by virtue of different cross section areas of their respective at least one internal fluid paths, and/or their differing respective pump capacities.

6. A bio-processing system including plural bioprocessing units each of claim 1 and a cassette holder configured to receive the or each cassette for supporting the cassette in use in a stack of said units.

7. The bio-processing system of claim 6, wherein the cassette holder and each cassette have complementary configurations for supplying power to the units and for proving a signal path to and/or from each unit in use.

8. The bio-processing system of claim 7, wherein the holder's complementary configurations supply electrical and/or pneumatic power and signal paths for each unit.

9. The modular bio-processing unit of claim 1, wherein the plural valves are configured to selectively divert flow relative to the at least one sensor element.

10. The modular bio-processing unit of claim 1, further comprising respective go/no-go membrane valves provided at each leg of a respective junction of the unit for controlling the direction of flow thereat.

* * * * *